United States Patent [19]
Badylak et al.

[11] Patent Number: 6,099,567
[45] Date of Patent: Aug. 8, 2000

[54] STOMACH SUBMUCOSA DERIVED TISSUE GRAFT

[75] Inventors: Stephen F. Badylak, West Lafayette; Sherry L. Voytik-Harbin, Zionsville; Andrew O. Brightman, West Lafayette; Robert S. Tullius, Brookston, all of Ind.

[73] Assignee: Purdue Research Foundation, West Lafayette, Ind.

[21] Appl. No.: 09/297,624

[22] PCT Filed: Dec. 10, 1997

[86] PCT No.: PCT/US97/23010

§ 371 Date: May 4, 1999

§ 102(e) Date: May 4, 1999

[87] PCT Pub. No.: WO98/25636

PCT Pub. Date: Jun. 18, 1998

Related U.S. Application Data

[60] Provisional application No. 60/032,683, Dec. 10, 1996.

[51] Int. Cl.[7] ................. A61F 2/08; A61F 35/37
[52] U.S. Cl. ................................ 623/13; 424/551
[58] Field of Search ................ 623/11, 13; 424/551

[56] References Cited

U.S. PATENT DOCUMENTS

| | | | |
|---|---|---|---|
| 4,902,508 | 2/1990 | Badylak et al. | 424/95 |
| 4,956,178 | 9/1990 | Badylak et al. | 424/551 |
| 5,275,826 | 1/1994 | Badylak et al. | 424/551 |
| 5,281,422 | 1/1994 | Badylak et al. | 424/551 |
| 5,352,463 | 10/1994 | Badylak et al. | 424/551 |
| 5,899,938 | 5/1999 | Sklar et al. | 623/13 |
| 5,922,027 | 7/1999 | Stone | 623/11 |

*Primary Examiner*—Michael J. Milano
*Assistant Examiner*—Hieu Phan
*Attorney, Agent, or Firm*—Barnes & Thornburg

[57] ABSTRACT

A tissue graft composition comprising stomach submucosal tissue delaminated from both the luminal portion of the tunica mucosa and the smooth muscle layers of the muscularis externa of a stomach of a warm blooded vertebrate is described. The graft composition can be or implanted into a host to replace or support damaged or diseased tissues.

13 Claims, No Drawings

STOMACH SUBMUCOSA DERIVED TISSUE GRAFT

CROSS-REFERENCES TO RELATED APPLICATIONS

This application is a U.S. national application of international application Ser. No. PCT/US97/23010 filed Dec. 10, 1997, which claims priority to U.S. Provisional application Ser. No. 60/032,683 filed Dec. 10, 1996.

FIELD OF THE INVENTION

The present invention relates to a tissue graft composition and methods for its preparation and use. More particularly, the present invention is directed to non-immunogenic tissue graft compositions comprising stomach submucosa and use of same to promote endogenous tissue growth.

BACKGROUND AND SUMMARY OF THE INVENTION

It is known that compositions comprising the tunica submucosa of the intestine of warm-blooded vertebrates can be used advantageously as tissue graft materials. See U.S. Pat. Nos. 4,902,508 and 5,281,422. The tissue graft compositions described in those patents are characterized by excellent mechanical properties, including a high burst pressure, and an effective porosity index which allows such compositions to be used beneficially for vascular graft and connective tissue graft constructs. When used in such applications the graft constructs appear not only to serve as a matrix for the regrowth of the tissues replaced by the graft constructs, but, indeed, promote or induce such regrowth of endogenous tissue. Common events to this remodeling process include: widespread and very rapid neovascularization, proliferation of granulation mesenchymal cells, biodegradation/resorption of implanted intestinal submucosal tissue material, and lack of immune rejection.

It is also known that intestinal submucosa can be fluidized by comminuting and/or enzymatic digestion, without loss of its apparent biotropic properties, for use in less invasive methods of administration (e.g., by injection or topical application) to host tissues in need of repair. See U.S. Pat. No. 5,275,826.

There has been much additional research effort directed to finding other natural and synthetic materials having the requisite properties for use as tissue grafts. Surprisingly, it has been found that stomach submucosa prepared by delamination of stomach tissue of warm-blooded vertebrates exhibits mechanical and biotropic properties similar to that which has been reported for intestinal submucosal tissue. It can be substituted for intestinal submucosa tissue in most, if not all, of the applications previously reported for intestinal submucosa.

The tissue graft composition of the present invention comprises stomach submucosa derived from stomach tissue of a warm-blooded vertebrate. The wall of the stomach is composed of the following layers: the tunica mucosa (including an epithelium layer, a tunica propria layer consisting of reticular or fine areolar tissue, and a glandular layer), the tunica submucosa layer (composed of areolar tissue and lacking glands), the tunica muscularis layer (composed of three layers of muscle), and the serosa (a layer of mesothelium outside the loose connective tissue which invests the muscle layers). Blood vessels, lymphatic tissue and neurological tissue also pervade the stomach tissues including the tunica submucosa.

Stomach submucosal tissue in accordance with the present invention compises stomach submucosa delarminated from the glandular portion of the tunica mucosa and the smooth muscle layers of the muscularis externa. The composition has proven to have the ability to induce connective tissue remodeling and wound healing in a fashion very similar to that of intestinal submucosa as described in U.S. Pat. No. 5,275,826. Specifically, the stomach submucosa composition causes cell proliferation in vitro, supports cell growth when used as a growth substrate material, and induces the formation and repair of connective tissue structures such as Achilles tendon when placed in xenogeneic host species. Stomach submucosa appears to be non-antigenic, and induces responses in vivo that are recognized components of wound healing such as neovascularization, cellular infiltration, deposition of extracellular matrix, and eventual degradation and replacement of the implanted material with host tissues. The present graft composition can be implanted or injected into a vertebrate host to induce the repair or replacement of damaged or defective tissues.

DETAILED DESCRIPTION OF THE INVENTION

The tissue graft composition in accordance with the present invention comprises stomach submucosa of a warm-blooded vertebrate delaminated from adjacent stomach tissue layers. The present tissue graft composition thus comprises the stomach submucosa delaminated from the smooth muscle layers of the muscularis externa and at least the luminal portion of the mucosal layer of a segment of the stomach of a warm-blooded vertebrate. In one embodiment, the stomach submucosal tissue compositions comprise the tunica submucosa and basilar portions of the tunica mucosa of the stomach of a warm blooded vertebrate. Typically the delamination technique described below provides a tissue composition consisting essentially of stomach submucosa. Those compositions are referred to herein generically as stomach submucosal tissue.

The glycosaminoglycan (GAG) content of stomach submucosa has been analyzed. The types of GAGs identified in stomach submucosa include heparin, chondroitin sulfate A, chondroitin sulfate B, and hyaluronic acid. In contrast to intestinal submucosa, heparan sulfate was not found in stomach submucosa.

The amount of water present in a sample of stomach submucosa, varies dependent upon the processing steps utilized after the delamination of the tissue. In accordance with one procedure the material was left to "drain" itself of water by sitting on a solid surface for ten minutes. The weight of the material was then determined, and the material was subjected to a mechanical wringer to remove additional excess water before freezing and lyophilization. Repeated measurements on two separate specimens showed a water content which ranged from about 80% to about 94%. The degree of variability is undoubtedly due to the variability of determining the initial "wet weight". However, it can be safely said that the water content of stomach submucosa is between 80 and 95%.

The stomach submucosa composition of this invention is typically prepared from stomach tissue harvested from animals raised for meat production, including, for example, pigs, cattle and sheep or other warm-blooded vertebrates. This tissue is normally a discarded by-product of meat processing. Thus, there is an inexpensive commercial source of stomach tissue for use in preparation of the tissue compositions in accordance with the present invention.

The preparation of stomach submucosa from a segment of stomach is similar to the procedure for preparing intestinal submucosa detailed in U.S. Pat. No. 4,902,508, the disclosure of which is expressly incorporated herein by reference. A segment of stomach tissue is first subjected to abrasion using a longitudinal wiping motion to remove the outer layers (particularly the smooth muscle layers) and the luminal portions of the tunica mucosa layers. The resulting submucosa tissue has a thickness of about 100 to about 200 micrometers, and consists primarily (greater than 98%) of acellular, eosinophilic staining (H&E stain) extracellular matrix material. Occasional blood vessels and spindle cells consistent with fibrocytes are scattered randomly throughout the tissue. Typically the submucosa is rinsed with water for approximately 2 hours and optionally stored in a frozen hydrated state until used as described below. Delamination of the tunica submucosa from both the muscularis externa and at least the luminal portions of the tunica mucosa layers and rinsing of the submucosa provides an acellular stomach submucosal tissue matrix.

Fluidized stomach submucosa can be prepared in a manner similar to the preparation of fluidized intestinal submucosa, as described in U.S. Pat. No. 5,275,826 the disclosure of which is expressly incorporated herein by reference. The submucosa tissue is comminuted by tearing, cutting, grinding, shearing and the like. Grinding the submucosa in a frozen or freeze-dried state is preferred although good results can be obtained as well by subjecting a suspension of submucosa pieces to treatment in a high speed (high shear) blender and dewatering by centrifuging and decanting excess water. Additionally, the conmuinuted fluidized tissue can be solubilized by enzymatic digestion of the stomach submucosa including the use of proteases, such as trypsin or pepsin, or other appropriate enzymes such a collagenase or a glycosaminoglycanase, or the use of a mixture of enzymes, for a period of time sufficient to solubilize said tissue and form a substantially homogeneous solution.

The present invention also contemplates the use of powder forms of stomach submucosa. In one embodiment a powder form of stomach submucosa is prepared by pulverizing stomach submucosal tissue under liquid nitrogen to produce particles ranging in size from 0.1 to 1 $mm^2$. The particulate composition is then lyophilized overnight and sterilized to form a solid substantially anhydrous particulate composite. Alternatively, a powder form of stomach submucosa can be formed from fluidized submucosa by drying the suspensions or solutions of comminuted and/or partially digested stomach submucosa.

The stomach submucosal tissue compositions of the present invention lend themselves to a wide variety of surgical applications relating to the repair or replacement of damaged tissues, including, for example the repair of vascular and connective tissues. Connective tissues for the purposes of the present invention includes bone, cartilage, muscle, tendons, ligaments, and fibrous tissue including the dermal layer of skin.

In accordance with the present invention, stomach submucosal tissue is used to prepare tissue graft compositions that are useful for inducing the formation of endogenous tissue at a desired site in a warm blooded vertebrate. Compositions comprising stomach submucosa can be administered to a vertebrate host in an amount effective to induce endogenous tissue growth at a site in the host in need of same due to the presence of damaged or diseased tissue. The stomach submucosa compositions can be administered to the host in either solid or sheet form, by surgical implantation alone or in combination with other art-recognized implant compositions, or in fluidized form, by injection.

In one embodiment the present stomach submucosa compositions in sheet form can be used to form vascular grafts. The diameter of the graft should be about the same as the diameter of the recipient blood vessel. This is accomplished by manipulating the stomach submucosa to define a cylinder having diameter approximately the same as that of the recipient blood vessel and suturing or otherwise securing the tissue graft longitudinally to form said vascular graft. Thus, for example, a vascular graft can be prepared by selecting a sterile glass rod having an outer diameter equal to that of the recipient blood vessel, wrapping the stomach submucosa sheet around the glass rod and gathering the redundant tissue. The desired lumen diameter is achieved by suturing along the length of the graft (for example, using two continuous suture lines or a simple interrupted suture line) or by using other art-recognized tissue securing techniques. The vascular graft is surgically substituted for a damaged or diseased blood vessel using standard vascular surgery techniques.

Consistent with the use of stomach submucosa as a vascular graft material, stomach submucosa possesses mechanical properties similar to those of intestinal submucosa and highly desirable for such tissue graft materials, including low porosity index and a high burst pressure. Those skilled in the art will appreciate that vascular graft material must be of low enough porosity to prevent intraoperative hemorrhage and yet of high enough porosity to allow extension of a newly-developed vasa vasorum through the graft material to nourish the luminal surface.

The present stomach submucosa segments can also be used in accordance with this invention as a tissue graft construct for use in the repair or replacement of connective tissues using the same procedures described for use of intestinal submucosa in U.S. Pat. Nos. 5,281,422 and 5,352,463, the disclosures of which are expressly incorporated herein by reference. The stomach submucosa composition can be used in its delaminated natural sheet form or it can be cut longitudinally or laterally to form elongated tissue segments. Such segments have an intermediate portion, and opposite end portions and opposite lateral portions which can be formed for surgical attachment to existing physiological structures, using surgically acceptable techniques.

The grafts formed and used in accordance with this invention, upon implantation, undergo biological remodeling. They serve as a rapidly vascularized matrix for support and growth of new endogenous connective tissue. When used as a tissue graft material stomach submucosa has been found to be trophic for host tissues with which it is attached or otherwise associated in its implanted environment. The graft material has been found to be remodelled (resorbed and replaced with autogenous differentiated tissue) to assume the characterizing features of the tissue(s) with which it is associated at the site of implantation.

Applicants anticipate that stomach submucosa can be used for tendon and ligament replacement and repair as has been previously described for intestinal submucosa. Furthermore, for tendon and ligament replacement applications, and other connective tissue repair applications the stomach submucosa material will typically be conditioned, as described in U.S. Pat. No. 5,275,826 (the disclosure of which is expressly incorporated herein by reference) to alter the viscoelastic properties of the submucosal tissue and reduce the strain of the originally isolated stomach submucosal tissue. The term strain as used herein refers to the maximum amount of tissue elongation before failure of the tissue, when the tissue is stretched under an applied load. It is expressed as a percentage of the length of the tissue before loading. In accordance with one embodiment stomach submucosa delaminated from both the luminal portion of the tunica mucosa and the smooth muscle layers of the muscularis externa of a stomach of a warm blooded vertebrate is conditioned to have a strain of no more than 20%. The submucosal tissue is conditioned by stretching, chemically treating, enzymatically treating or exposing the tissue to other environmental factors.

In one embodiment the strips of stomach submucosa tissue are conditioned by stretching the submucosa tissue longitudinally to form a graft construct having a length longer than the length of the stomach submucosa from which the graft construct was formed, and more particularly, by stretching in a longitudinal or lateral direction so that the strips of intestinal submucosa tissue have a strain of no more than 20%.

One method of "conditioning" the tissue by stretching involves applying a given load to the stomach submucosa for three to five cycles. Each cycle consists of applying a load to the graft material for five seconds, followed by a ten second relaxation phase. Three to five cycles will produce a stretch-conditioned graft material with reduced strain. The graft material does not return to its original size; it remains in a "stretched" dimension. For example, a stomach submucosa segment can be conditioned by suspending a weight from said segment, for a period of time sufficient to produce a tissue having a strain of less than 20%, for example, about 10 to about 20%. Optionally, the graft material can be preconditioned by stretching in the lateral dimension. The graft material exhibits similar viscoelastic properties in the longitudinal and lateral dimensions.

The graft segment is then formed, in accordance with one embodiment, in a variety of shapes and configurations, for example, to serve as a ligament or tendon replacement or a patch for a broken or severed tendon or ligament. The segment can be shaped and formed to have a layered or even a multilayered configuration with at least the opposite end portions and/or opposite lateral portions being formed to have multiple layers of the graft material to provide reinforcement for attachment to physiological structures, including bone, tendon, ligament, cartilage and muscle. In ligament replacement applications, opposite ends can be attached using standard surgical techniques to first and second bones, respectively, with the bones typically being articulated as in the case of a knee joint.

The end portions of the stomach submucosa composition can be formed, manipulated or shaped to be attached, for example, to a bone structure in a manner that will reduce the possibility of graft tearing at the point of attachment. Preferably the material can be folded or partially everted to provide multiple layers for gripping, for example, with spiked washers or staples.

Alternatively, the stomach submucosa composition may be folded back on itself to join the end portions to provide a first connective portion to be attached, for example, to a first bone and a bend in the intermediate portion to provide a second connective portion to be attached to a second bone articulated with respect to the first bone. For example, one of the end portions may be adapted to be pulled through a tunnel in, for example, the femur and attached thereto, while the other of the end portions may be adapted to be pulled through a tunnel in the tibia and attached thereto to provide a substitute for the natural cruciate ligament, the segment being adapted to be placed under tension between the tunnels to provide a ligament function, i.e., a tensioning and positioning function provided by a normal ligament.

Multiple strips/pieces of stomach submucosa can be overlapped and compressed, under conditions allowing dehydration of the tissue, to fuse the strips/pieces of the stomach submucosal tissue into a unitary multi-laminate construct. It is anticipated that the process for forming the intestinal submucosa constructs described in U.S. patent application Ser. No. 08/418,515 (the disclosure of which is expressly incorporated herein by reference) are applicable to stomach submucosa and can be used to form multi-laminate constructs of stomach submucosa.

The present stomach submucosa compositions may be sterilized using conventional sterilization techniques including tanning with glutaraldehyde, formaldehyde tanning at acidic pH, ethylene oxide treatment, propylene oxide treatment, gas plasma sterilization, gamma radiation, and peracetic acid sterilization. A sterilization technique which does not significantly weaken the mechanical strength and biotropic properties of the graft is preferably used. For instance, it is believed that strong gamma radiation may cause loss of strength in the graft material. Because one of the most attractive features of the graft constructs formed from stomach submucosal tissue is their ability to induce host-remodelling responses, it is desirable not to use a sterilization approach which will detract from that property. Preferred sterilization techniques include exposing the graft to peracetic acid, low dose gamma irradiation ($\leq 2.5$ mRad) and gas plasma sterilization; peracetic acid sterilization being the most preferred method. Typically, after the tissue graft composition has been sterilized, the composition is wrapped in a non-porous plastic wrap and sterilized again using ethylene oxide or gamma irradiation sterilization techniques.

The stomach submucosal tissue compositions of the present invention can also be used in accordance with this invention in a method and composition for supporting the proliferation and inducing differentiation of eukaryotic cells cultured in vitro. Procedures for utilizing submucosal tissue for the in vitro culturing of cells is described in U.S. patent application Ser. No. 08/386,452, the disclosure of which is expressly incorporated herein. Generally the method comprises the step of contacting eukaryotic cells, in vitro, with a vertebrate stomach submucosa-derived matrix under conditions conducive to eukaryotic cell growth.

In one embodiment a eukaryotic cell culture substrate is prepared comprising submucosal tissue. The submucosal tissue can be combined with various nutrients, growth factors, minerals and salts know by those skilled in the art to be important in cell culture procedures. The term "contacting" as used herein with reference to cell culture is intended to include both direct and indirect contact, for example in fluid communication, of the submucosal tissue and the cultured cells. The term "conditions conducive to eukaryotic cell growth" as used herein refers to the environmental conditions, such as sterile technique, temperature and nutrient supply, that are considered optimal for eukaryotic cell growth under currently available cell culture procedures. Although optimum cell culture conditions used for culturing eukaryotic cells depend somewhat on the particular cell type, cell growth conditions are generally well known in the art.

Furthermore, stomach submucosal tissue can be combined with current available cell culture media to enhance the effectiveness of such media to induce growth, proliferation and differentiation of various cell types.

EXAMPLE 1

Preparation of Stomach Submucosal Tissue

The tissue graft material of this invention is prepared in accordance with the following steps:

The stomach is first removed from the animal source by cutting the esophagus and small intestine at their respective entrance and exit points on the stomach. Any excess mesentery tissue or fat is removed from the stomach and the contents of the stomach are emptied and any remaining residues are removed from the inside of the stomach by rinsing with running tap water. The stomach is then everted to expose the inside layers of the stomach. The portions of the stomach that begin to form the entrance or exit points of the stomach are removed. The stomach is typically left whole, however the stomach can also be cut and flattened prior to removal of unwanted tissues.

The luminal surface of the stomach is subject to abrasion using the handle portion of a pair of scissors or hemostats to scrape off the inner layers of the stomach including at least the luminal portion of the tunica mucosa. A thin residual layer will remain at this point. If the tissue was left whole, the stomach tissue is everted again to return the luminal surface of the stomach to the interior of the graft construct. A small cut is then made in the exterior muscle fiber layer. The muscle layers are then delaminated from the submucosal tissue through the use of a pair of scissors or hemostat to enlarge the cut in the muscle and scrape off the muscle layers. The remaining tissue is everted again to place the luminal side on the exterior of the tissue graft. The luminal surface is scraped to remove the remaining inside residue which has a brownish color. The stomach tissue is scraped until the tissue appears pinkish-white in color.

During the preparation of the stomach tissue care is taken to keep the tissue moist by periodically hydrating the tissue with water. The stomach submucosal tissue is rinsed in running tap water for approximately two hours to remove any blood or loose tissue scrapings and lyse and remaining cells. After rinsing the tissue should appear white, if the tissue remains pinkish in color the tissue is rubbed under water until the tissue appears white. After rinsing is complete excess water is removed by ringing the tissue by hand or the use of mechanical ringers. The tissue is then stored in liquid nitrogen at −80° C.

EXAMPLE 2

Mechanical Properties of Stomach Submucosa

The mechanical properties of stomach submucosa biomaterial has been evaluated using two different bench top tests: the "wet diaphragm burst test" and the "ball burst test".

The wet diaphragm burst test involves the placement of the material in an aperture to form a "diaphragm" comprising submucosa tissue held by a surrounding ring. Water pressure is applied to one side of the material until the point of failure. The accumulated data from 10 separate test samples of each material is presented in Table 1, comparing the wet diaphragm burst test of intestinal submucosa, urinary bladder submucosa, and stomach submucosa. The terms "in medium" and "frozen" indicate the method by which the materials were stored subsequent to harvesting and prior to testing.

TABLE 1

Wet Diaphragm Burst Test (Pressure, in $Kg/cm^2$)

| Sample # | Intestinal Submucosa in Medium | Urinary Bladder Submucosa in Medium | Urinary Bladder Submucosa Frozen | Stomach Submucosa in Medium | Stomach Submucosa Frozen |
|---|---|---|---|---|---|
| 1 | 1.173 | 0.107 | 0.391 | 2.264 | 0.723 |
| 2 | 0.992 | 0.141 | 0.548 | 2.011 | 1.130 |
| 3 | 0.880 |  | 0.439 | 2.148 | 0.905 |
| 4 | 1.350 |  | 0.343 | 2.444 | 1.234 |
| 5 | 1.313 |  | 0.455 | 2.382 | 1.094 |
| 6 | 0.692 |  | 0.574 | 2.463 | 1.403 |
| 7 | 0.810 |  | 0.602 | 2.474 | 0.959 |
| 8 | 0.987 |  | 0.354 | 2.882 | 1.198 |
| 9 | 0.942 |  | 0.498 | 2.275 | 0.703 |
| 10 | 0.827 |  | 0.275 | 2.415 | 1.603 |
| Average | 0.990 | 0.124 | 0.448 | 2.376 | 1.095 |
| Stan. Deviation | 0.2196 | 0.0239 | 0.0108 | 0.2329 | 0.2850 |

The strength of stomach submucosal tissue grafts can also be determined through the use of a material testing system (MTS) tensile tester. The stomach submucosal tissue sheet is secured within a circular clamp (specimen clamp) to provide uniform distribution of the stress through out the tissue sheet. The handle of the specimen clamp is lifted to its topmost position so that the jaws of the clamp are able to accept the test specimen. The submucosal tissue construct is cut to fit the specimen clamp, the aperture of the clamp having a diameter of one and nine sixteenths (4 cm). Approximately 1.3–1.5 cm of excess material should be included around the perimeter of the test specimen to ensure sufficient clamping area. The submucosal tissue is placed in jaws of the clamp and secured, the clamp force being controlled by thumbwheel means located on the top clamp.

The initial fixture level is set so that the top of the steel ball is located immediately under the plane the test specimen. The metal ball forced up against the clamped submucosal tissue at a controlled rate utilizing a tensile tester software interface to control and measure the force placed on the test specimen. The force is increased until failure of the specimen occurs. Failure is defined as the maximum load which corresponds to the first appearance of the ball through visible non-natural discontinuities in the plane of the specimen. In the case that the topmost position of the fixture is reached prior to failure, the software limits will engage and discontinue the test. The peak load value displayed on the Microprofiler 458.01 is recorded and the specimen is removed. Table 2 presents the accumulated data of the ball burst test comparing three different sources of submucosa: intestinal submucosa, urinary bladder submucosa and stomach submucosa. These results demonstrate that stomach submucosa is the strongest of these three different biomaterials.

TABLE 2

Ball burst test (maximum load in Kg)

| Intestinal Submucosa | Urinary Bladder Submucosa | Stomach Submucosa |
| --- | --- | --- |
| 2.05 ± 0.05 | 1.57 ± 0.05 | 8.62 ± 3.06 |

EXAMPLE 3

In-Vivo Remodeling

Sections of stomach submucosa, were used as a scaffold to replace portions of excised urinary bladder in the dog. Two experiments were done. One animal was sacrificed after three weeks and the second animal was sacrificed after six weeks. The morphologic evaluation of the remodeled tissues showed growth of transitional epithelium over the surface of the stomach submucosa scaffold and the presence of smooth muscle cells within the bioscaffold. Because there was no definitive way of identifying the presence or absence of remaining stomach submucosa, the degree and/or extent of degradation of stomach submucosa cannot be determined from these studies.

EXAMPLE 4

In-vitro Cell Growth Properties of Stomach Submucosa

The ability of stomach submucosa to serve as an extracellular matrix to support in-vitro cell growth was tested by applying several cell types to the stomach submucosal tissue surface under standard cell culture conditions. The cell types tested included 3T3 fibroblasts, intestinal epithelium cells and FR (fetal rat) mesenchymal cells. All three cell types showed the ability to proliferate readily upon this extracellular matrix without the addition of the supplements that would be needed to grow these cells on a plastic surface. Therefore, it can be concluded that the material contains necessary structure and composition "nutrients" to serve as a cell culture substrate for supporting cell growth.

What is claimed is:

1. A composition capable of inducing the formation of endogenous tissue when implanted at a site in need of endogenous tissue growth comprising stomach submucosa delaminated from both the luminal portion of the tunica mucosa and the smooth muscle layers of the muscularis externa of a stomach of a warm blooded vertebrate.

2. The composition of claim 1 wherein the stomach submocosa is fluidized.

3. The composition of claim 1 wherein the stomach submucosa is digested with an enzyme for a period of time sufficient to solubilize the stomach submucosa and provide a substantially homogenous solution.

4. The composition of claim 2, wherein the stomach submucosais dried and in powder form.

5. The composition of claim 1 formed into a cylinder having a predetermined luminal diameter and sutured along the length of the cylinder.

6. The composition of claim 1 conditioned to reduce the strain of the isolated stomach submucosa for use as a connective tissue substitute.

7. The composition of claim 6 wherein the stomach submucosa is conditioned by stretching to produce a graft construct longer in at least one dimension than the stomach submucosa from which it is formed.

8. The use of stomach submucosa for the preparation of a tissue graft construct useful for inducing endogenous tissue growth when implanted in warm-blooded vertebrates, said stomach submucosa being delaminated from both the luminal portion of the tunica mucosa and the smooth muscle layers of the muscularis externa of a stomach of a warm blooded vertebrate.

9. The use according to claim 8 wherein the stomach submucosa is in fluidized form.

10. The use according to claim 8 wherein the stomach submucosa is in powder form.

11. A method for inducing the formation of endogenous tissue at a site in need of endogenous tissue growth in a warm blooded vertebrate, said method comprising contacting said site with a graft composition comprising stomach submucosa in an amount effective to induce endogenous tissue growth at the site the composition is administered.

12. The method of claim 11, wherein the graft composition is fluidized and is administered by injection into the warm-blooded vertebrate.

13. The method of claim 12, wherein the graft composition is administered by surgically implanting the composition into the warm-blooded vertebrate.

* * * * *